(12) United States Patent
Muderlak et al.

(10) Patent No.: US 9,453,330 B2
(45) Date of Patent: Sep. 27, 2016

(54) FIXTURE CLEANING AND DEODORIZING APPARATUS AND METHOD OF USE

(71) Applicant: Xela Innovations, LLC, Glendale, WI (US)

(72) Inventors: Todd J. Muderlak, Whitefish Bay, WI (US); Kenneth J. Muderlak, Milwaukee, WI (US)

(73) Assignee: XELA INNOVATIONS, LLC, Glendale, WI (US)

( * ) Notice: Subject to any disclaimer, the term of this patent is extended or adjusted under 35 U.S.C. 154(b) by 629 days.

(21) Appl. No.: 13/842,659

(22) Filed: Mar. 15, 2013

(65) Prior Publication Data

US 2014/0115766 A1    May 1, 2014

Related U.S. Application Data

(60) Provisional application No. 61/719,638, filed on Oct. 29, 2012.

(51) Int. Cl.
*E03D 9/03* (2006.01)
*A61L 9/12* (2006.01)

(52) U.S. Cl.
CPC .............. *E03D 9/031* (2013.01); *A61L 9/122* (2013.01); *A61L 9/125* (2013.01); *A61L 9/127* (2013.01); *A61L 2209/111* (2013.01); *A61L 2209/133* (2013.01); *Y10T 29/4973* (2015.01)

(58) Field of Classification Search
CPC ..................................................... E03D 9/031
USPC .......................................... 422/306; 4/226.1
See application file for complete search history.

(56) References Cited

U.S. PATENT DOCUMENTS

| 5,114,625 | A |   | 5/1992  | Gibson |
|-----------|---|---|---------|--------|
| 5,249,718 | A |   | 10/1993 | Muderlak |
| 5,449,117 | A | * | 9/1995  | Muderlak .............. A47K 17/00 222/646 |
| 7,157,057 | B2 |   | 1/2007  | Gohil |
| 7,244,398 | B2 |   | 7/2007  | Kotary et al. |
| 7,922,104 | B2 |   | 4/2011  | Zlotnik et al. |
| 8,157,188 | B2 |   | 4/2012  | Duston et al. |
| 2004/0265189 | A1 |   | 12/2004 | Schwarz |
| 2006/0163376 | A1 |   | 7/2006  | Lakatos et al. |

(Continued)

FOREIGN PATENT DOCUMENTS

DE    9402313 U1    3/1994
EP    0365770 A1    5/1990

(Continued)

OTHER PUBLICATIONS

International Preliminary Report on Patentability and Written Opinion for International Application No. PCT/US2013/067131 dated May 5, 2015, 11 pages.

(Continued)

*Primary Examiner* — Sean E Conley
(74) *Attorney, Agent, or Firm* — Husch Blackwell LLP

(57) ABSTRACT

A fixture cleaning and deodorizing apparatus including a container assembly with a wick assembly and a solution container, wherein the wick assembly is secured to at least one of the solution container and a dispenser, the dispenser receives at least one of the container assembly and solution container therein, and the dispenser is configured to dispense solution from the solution container; and a fan assembly situated in the dispenser.

16 Claims, 19 Drawing Sheets

(56) References Cited

U.S. PATENT DOCUMENTS

| | | |
|---|---|---|
| 2006/0180143 A1 | 8/2006 | Lind et al. |
| 2007/0036673 A1 | 2/2007 | Selander |
| 2009/0151061 A1 | 6/2009 | Chen |
| 2010/0147972 A1 | 6/2010 | Lakatos et al. |
| 2013/0032641 A1 | 2/2013 | Muderlak et al. |
| 2013/0034444 A1 | 2/2013 | Muderlak et al. |

FOREIGN PATENT DOCUMENTS

| | | |
|---|---|---|
| EP | 2564878 A1 | 3/2013 |
| WO | 2012/175972 A1 | 12/2012 |

OTHER PUBLICATIONS

International Search Report and Written Opinion for International Application No. PCT/US2013/067131 dated May 16, 2014, 16 pages.

Communication Relating to the Results of the Partial International Search for PCT/US2013/067131, mailing date Feb. 25, 2014, 2 pages.

International Preliminary Report on Patentability for International Application No. PCT/US2014/030123 dated Sep. 15, 2015, 12 pages.

* cited by examiner

FIXTURE CLEANING AND DEODORIZING APPARATUS AND METHOD OF USE

FIELD

This invention relates fixture cleaning and deodorizing devices, and specifically to a fixture cleaning device with a replaceable wick assembly and solution container.

BACKGROUND

Fixture cleaning and deodorizing devices are commonly utilized to address issues related to fixtures, such as toilets and urinals. These devices can include a liquid solution having one or more of deodorizers, cleaners, and fragrances. The solution is commonly provided via a supply tube from a container mounted to the device. The solution is pumped into a tube that passes the liquid solution either directly down an output tube or into a reservoir area. The solution then passes into a spurge pipe (or other inlet) connected to the fixture. The device can also hang over the fixture and drip into or onto the fixture. When affixed to a fixture, flushing of the device pulls the solution into (through) the spurge pipe and ultimately to the fixture to mix with incoming water and liquid and/or solid waste in the fixture. The solution is provided at a predetermined or intermittent rate or during a flushing action. In some devices, a wick is provided at the reservoir to absorb the solution and position it to receive a greater exposure to airflow. Over time it is common for the wick to develop a layer of solidified/crystalized solution thereupon. Eventually, the solidified/crystalized solution limits the wick's ability to wick (capillary action) the solution and/or expose the solution to airflow and therefore the device begins to fail in its intended operation and can lead to overflowing of the reservoir area. Periodic maintenance of the wick is required to maintain acceptable operation. Such maintenance requires a person to physically engage the wick, which can often be overlooked, and to remove it, which is often a messy and unpleasant operation. If a wick is left unchanged long enough, the device may require servicing to operate properly again. As such, maintenance is unpleasant, and often these devices are not properly maintained.

Accordingly, it would be desirable to provide a fixture cleaning and deodorizing apparatus and method of use that overcomes at least some of these shortcomings.

BRIEF SUMMARY

In at least one embodiment, the fixture cleaning and deodorizing apparatus includes a container assembly that includes a wick assembly and a solution container, wherein the wick assembly is secured to at least one of the solution container and a dispenser, wherein the dispenser receives at least one of the container assembly and solution container therein, and wherein the dispenser is configured to dispense solution from the solution container; and a fan assembly situated in the dispenser.

In at least another embodiment, a fixture cleaning and deodorizing dispenser is provided that includes a dispenser housing; a housing cover securable to the dispenser housing; a housing supply tube; a dispenser chamber configured to receive a solution container; one or more ridges formed with or secured to the dispenser housing; one or more battery compartments; a printed circuit board; a hammer for at least indirectly engaging a valve assembly of a solution container; and an output port in communication with the housing supply tube.

In at least another embodiment, a wick assembly is provided that includes a plurality of spacers secured together to form a collapsible wick support structure; a neck mount portion secured to a first end of the wick support structure, the neck mount portion configured to secure to a solution container; one or more wicks; and a wick mount secured to a second end of the wick support structure, the wick mount configured to secure the one or more wicks thereto.

In at least another embodiment, a container assembly is provided that includes a solution container for housing a solution and a wick assembly further that includes a plurality of spacers hingedly secured together in an accordion-style configuration; a neck mount portion secured to a first of the plurality of spacers, the neck mount portion secured to the solution container; one or more wicks; and a wick mount secured to a last of the plurality of spacers, the wick mount configured to secure the one or more wicks thereto.

In at least another embodiment, a method of wick replacement for a fixture cleaning and deodorizing apparatus is provided that includes accessing a dispenser chamber of a dispenser; removing a first container assembly from the dispenser chamber; installing a second container assembly in the dispenser chamber, wherein the second container assembly includes a rear channel extending along a back of the solution container; providing a wick assembly having one or more wicks secured thereto; and actuating a plurality of spacers hingedly secured together to push the wicks downward along the rear channel.

Other embodiments, aspects, features, objectives and advantages of the fixture cleaning apparatus and method of use will be understood and appreciated upon a full reading of the detailed description and the claims that follow.

BRIEF DESCRIPTION OF THE DRAWINGS

Embodiments of the fixture cleaning and deodorizing apparatus and method of use are disclosed with reference to the accompanying drawings and are for illustrative purposes only. The fixture and deodorizing cleaning apparatus and method of use are not limited in application to the details of construction, use, or the arrangement of the components illustrated in the drawings. The fixture cleaning and deodorizing apparatus and method of use are capable of other embodiments, or of being practiced or carried out in other various ways. In the drawings.

DETAILED DESCRIPTION

Figure 1:
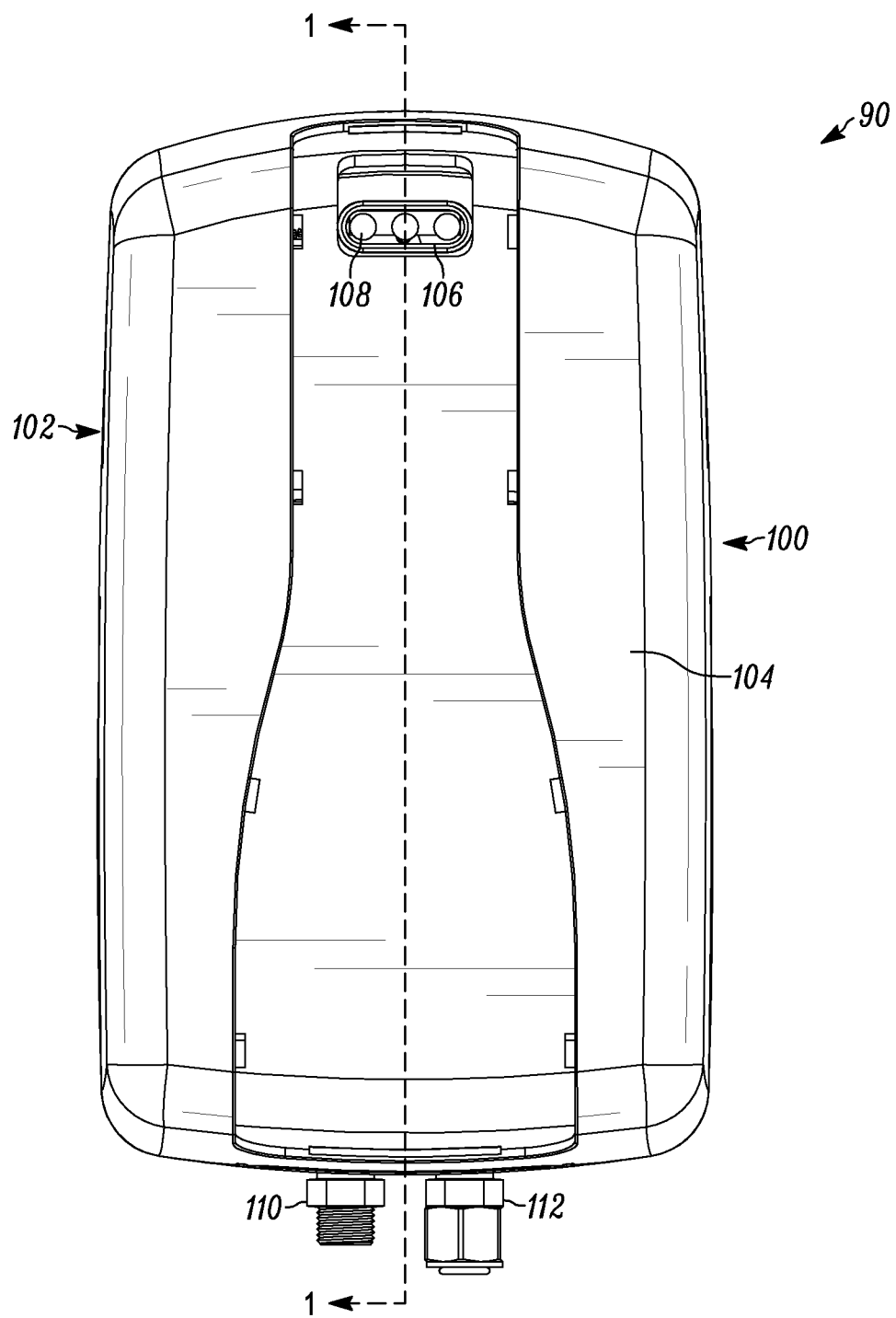
FIG. 1 illustrates a front view of an exemplary fixture cleaning and deodorizing apparatus that includes an exemplary dispenser and an exemplary container assembly.

Referring to FIG. 1, provided is a front view of an exemplary fixture cleaning and deodorizing apparatus 90, including a fixture cleaning and deodorizing dispenser 100 and a container assembly 122 (not shown) secured within the fixture cleaning and deodorizing dispenser 100. The apparatus 90 is configured to provide a metered amount of solution for use in one or more of deodorizing, cleaning, or scenting a plumbing fixture or the air in a bathroom. The solution can include one or more of various products, such as a deodorizer, cleaner, enzymes, bacteria, disinfectant, fragrance, etc.

The dispenser 100 includes a dispenser housing 102 and a housing cover 104. An indicator group 106 is provided that extends through or is positioned visibly behind the housing cover 104. Various sensors and/or LEDs 108 provide annunciation of operational status parameters, such as power on/off, battery charge low, refill low, etc. and sensing of various elements, such as motion, light, etc. Sensors can provide operational feedback for enhanced control of the fixture cleaning apparatus 90 and annunciating lights can provide essential information to maintenance personnel. In at least some embodiments, the fixture cleaning and deodorizing apparatus 90 further includes a primary output port 110 and a secondary output port 112. The output ports 110, 112 are each connected with a fixture such as a toilet, urinal, etc. In another embodiment, only the primary output port 110 is provided, and in yet another embodiment, neither output port is provided.

Figure 2:
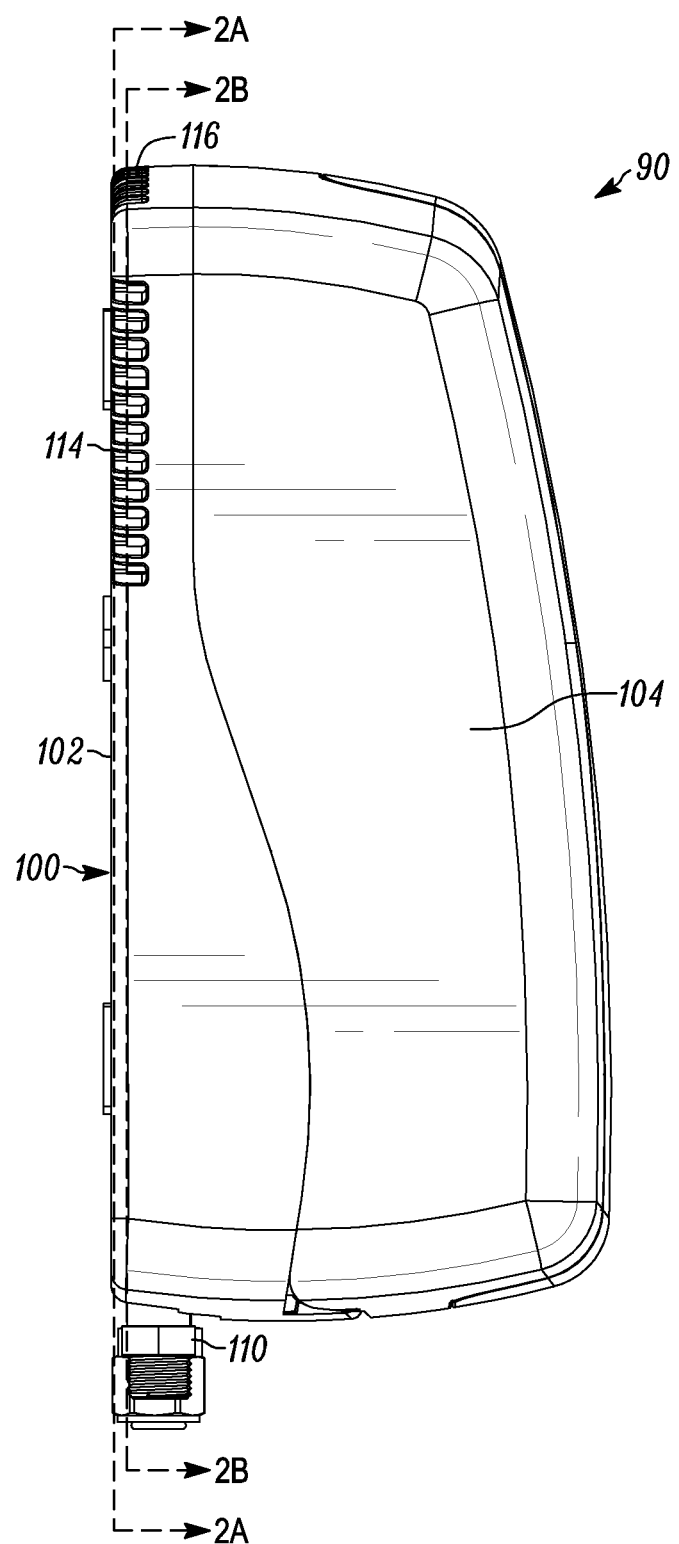
FIG. 2 illustrates a side view of the fixture cleaning and deodorizing apparatus of FIG. 1.
Figure 3:
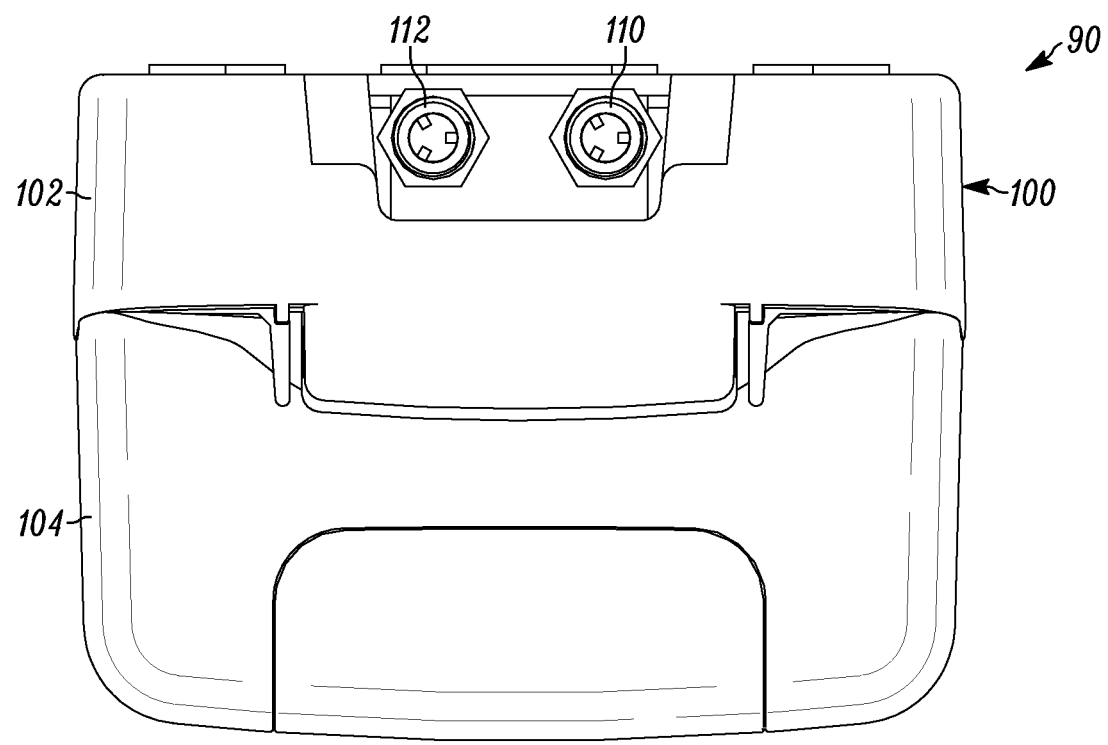
FIG. 3 illustrates a bottom view of the fixture cleaning and deodorizing apparatus of FIG. 1.
Figure 4:
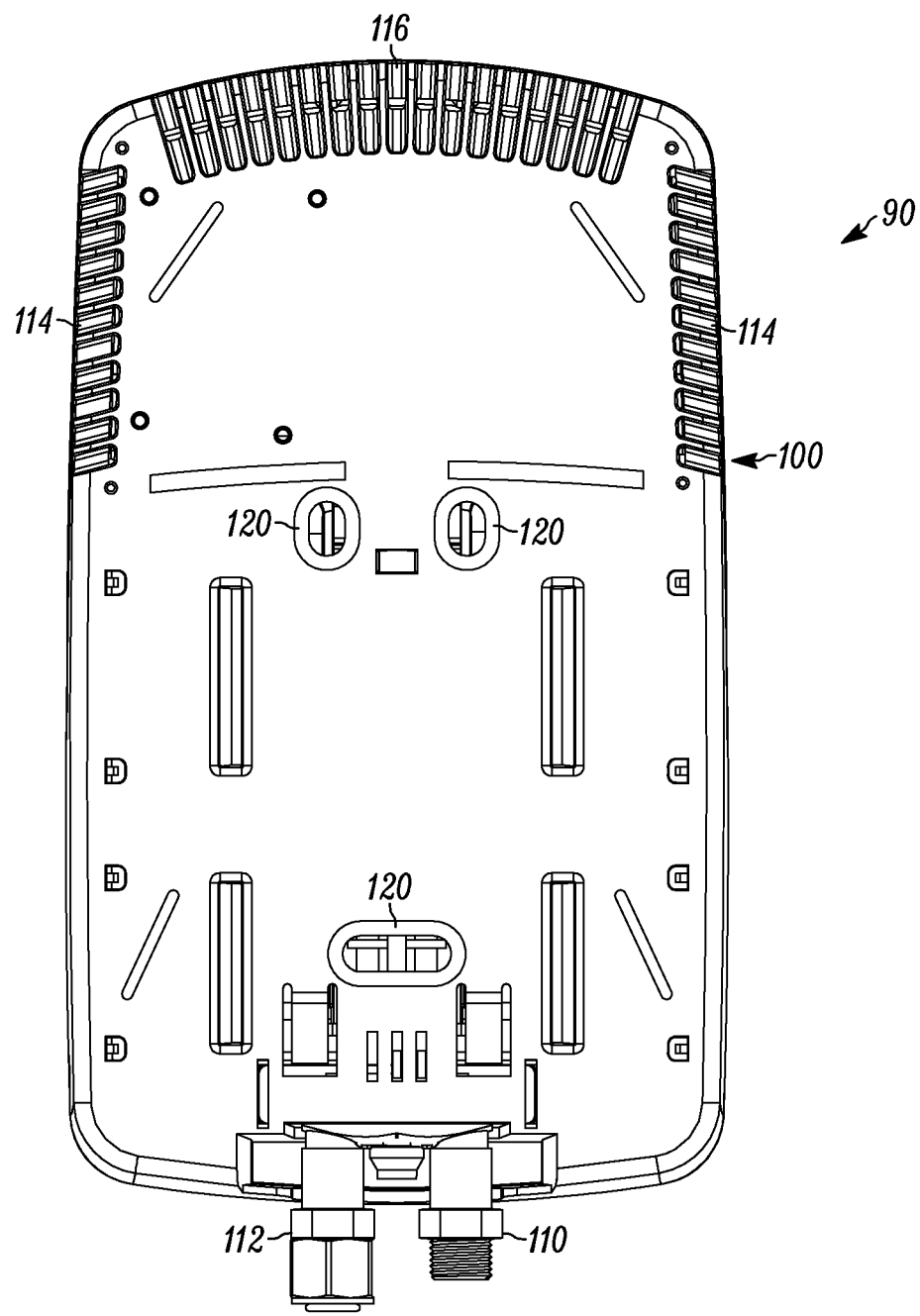
FIG. 4 illustrates a back view of the fixture cleaning and deodorizing apparatus of FIG. 1.

FIG. 2 illustrates a side view of the apparatus 90, displaying side intake vents 114 and top intake vents 116 formed in the dispenser housing 102. FIG. 3 illustrates a bottom view of the apparatus 90 with primary and secondary output ports 110, 112. FIG. 4 illustrates a back view of the apparatus 90 further illustrating the side intake vents 114 and top intake vents 116, as well as various securing points 120 for securing the apparatus 90 to a structure, such as a wall.

Figure 5A:
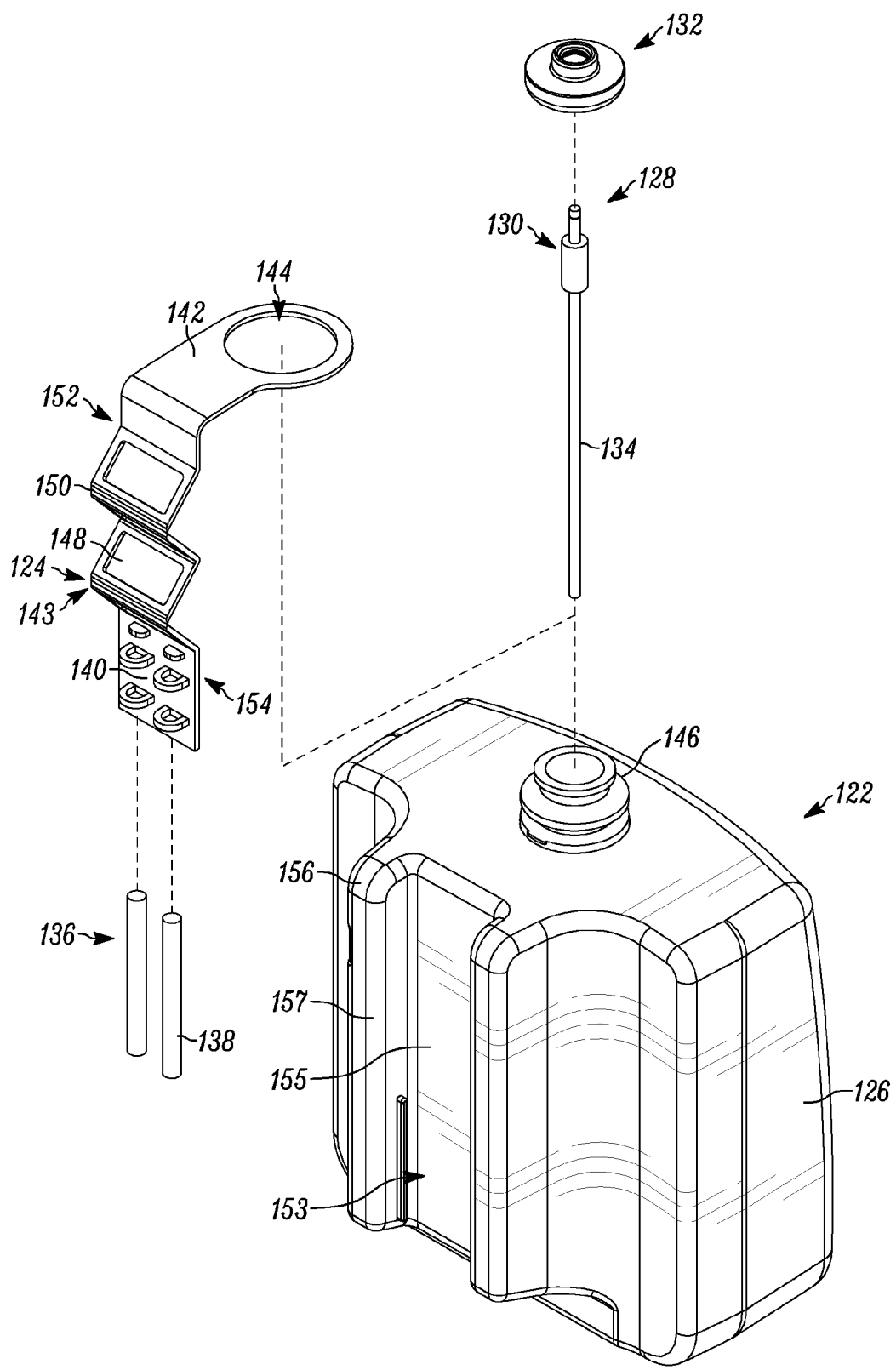
FIG. 5A illustrates an exploded perspective view of the container assembly including a wick support structure.
Figure 5B:
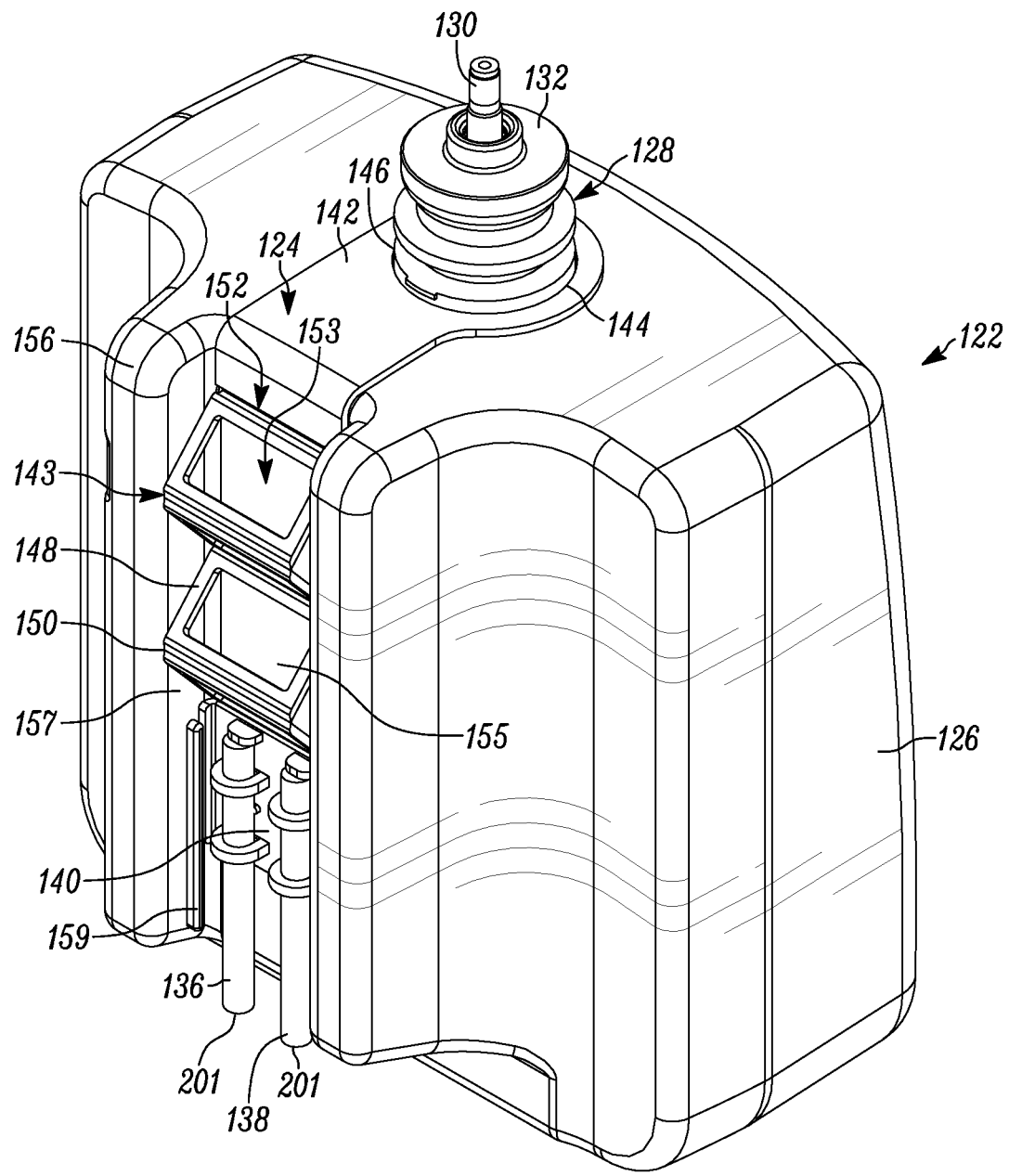
FIG. 5B illustrates the container assembly of FIG. 5A in a non-exploded view.
Figure 6:
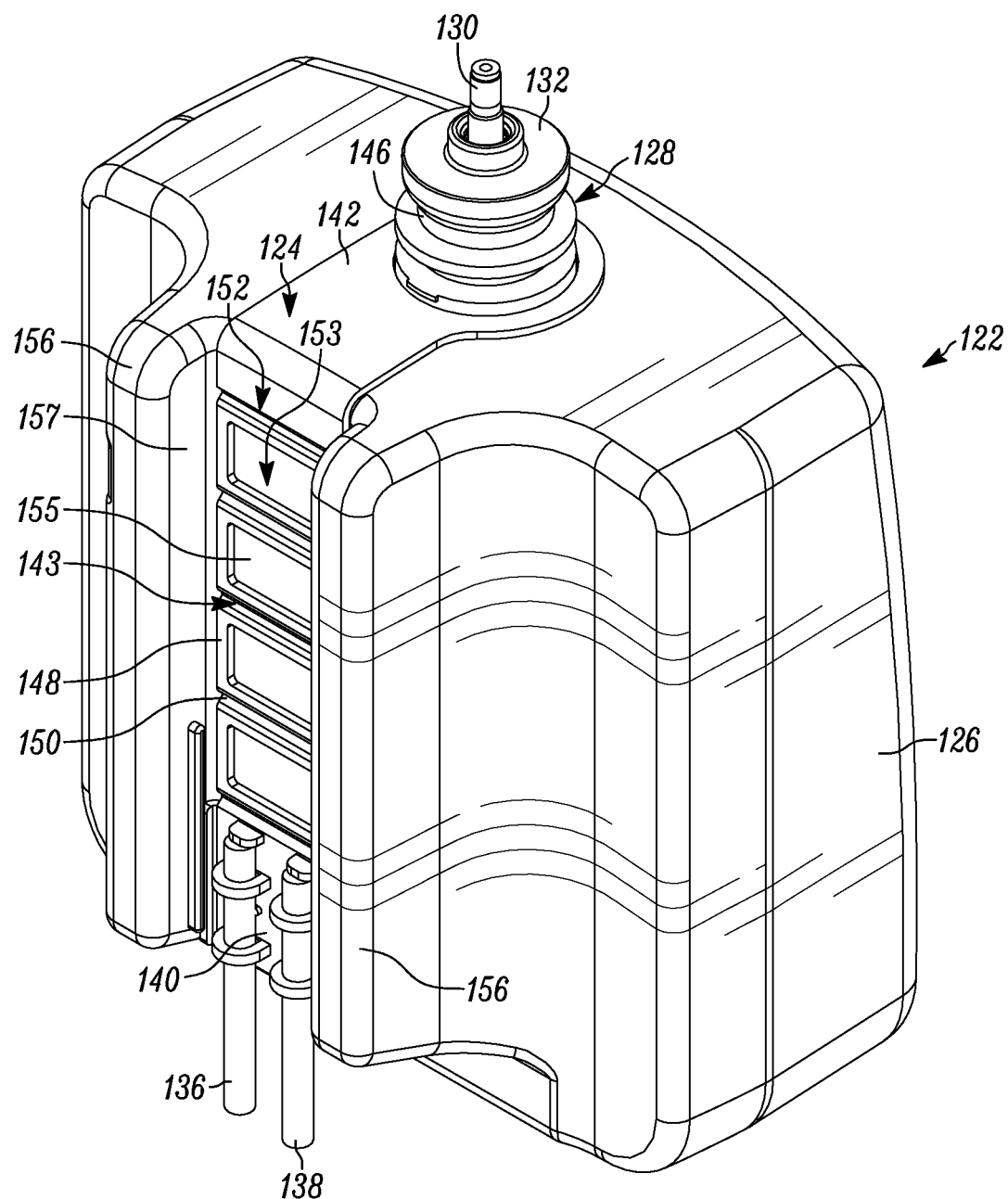
FIG. 6 illustrates a view of the container assembly with the wick support structure in an installation position.

Referring to FIGS. 5A and 5B, FIG. 5A illustrates an exploded perspective view of an exemplary container assembly 122 for use with the dispenser 100 of FIG. 1. FIG. 5B illustrates an assembled perspective view of the container assembly 122. As shown, the container assembly 122 includes a wick assembly 124, a solution container 126, and a pump valve assembly 128. The pump valve assembly 128 includes a pump 130, a fan assembly 240 (not shown), cap 132, and a container supply tube 134. The cap 132 secures the pump 130 to the solution container 126. The wick assembly 124 includes a neck mount portion 142 secured to a wick support structure 143. The neck mount portion 142 includes a passage 144 configured for receipt around a solution container neck 146. In the embodiment shown, neck mount portion has a circular aperture; however, neck mount portion may be any shape or structure to secure on container neck 146. Although not shown, other mechanisms can be provided in place of or in addition to the neck mount portion 142 to secure the wick assembly 124 to the solution container 126, such as an adhesive. The wick assembly 124 further includes one or more wicks, such as a primary wick 136 and a secondary wick 138, both secured to a wick mount 140, wherein the wick mount 140 is secured to the wick support structure 143. In at least some embodiments, the wick support structure 143 can be formed solely from the wicks 136, 138 themselves, thereby eliminating the need for an additional component. The wicks 136, 138 are shown as cylindrical with bottom portions 201, although other shapes can be provided, such as flat, rectangular, etc. The wick support structure 143 includes a plurality of interconnected structures, such as rigid or semi-rigid spacers 148, flexibly connected by hinges 150 to form a collapsible structure, such as an accordion-style folding structure. The spacers 148 are connected at a first end 152 to the neck mount portion 142 and at a second end 154 to the wick mount 140. Various portions of the wick assembly 124 are positioned at least partially in a rear channel 153 that extends vertically along the back of the solution container 126. The rear channel 153 includes a channel bottom portion 155 and side portions 157, which in sum, provide a path for directed movement of the spacers 148 and the wick mount 140. In addition, the side portions 157 of the rear channel 153 can include vertical rails 159 (FIG. 5B) that are positioned to support the wick mount 140 in the rear channel 153 to allow for vertical travel about the channel bottom portion 155, but to inhibit horizontal movement out away from the channel bottom portion 155. Although rails 159 are shown, other mechanisms such as tabs, channels, etc. can be utilized.

The solution container 126 is shaped and sized to fit inside the dispenser housing 102 with the housing cover 104 in a closed position, although other shapes and sized can be provided. The solution container 126 can include protrusions 156 and/or channels that are configured to matingly engage with mating channels or protrusions in the dispenser housing 102. In this regard, only a solution container 126 with matching channels and/protrusions can be installed in the dispenser housing 102. In addition, the mating channels and/protrusions can serve to secure the container assembly 122 to the dispenser housing 102. Further, the solution container can be formed from various types of materials, rigid, semi-rigid, and flexible, for example, a rigid wall plastic container, or a flexible plastic bag.

As seen in FIG. 5B, the spacers 148 are situated in an at least partially folded position in the container channel 153. When the container assembly 122 is installed in the dispenser housing 104, the spacers 148 are pushed into a flattened position, as discussed in greater detail below. FIG.

6 provides a view of the container assembly 122, wherein the unfolded positioning of the wick support structure 143 shown is representative of the positioning of the wick support structure 143 when the container assembly 122 is installed in the dispenser 100. More particularly, the spacers 148 have been unfolded into a flat position adjacent to the channel bottom portion 155 of the rear channel 153, thereby displacing in a downward direction the wick mount 140 along with the wicks 136, 138.

Figure 7:
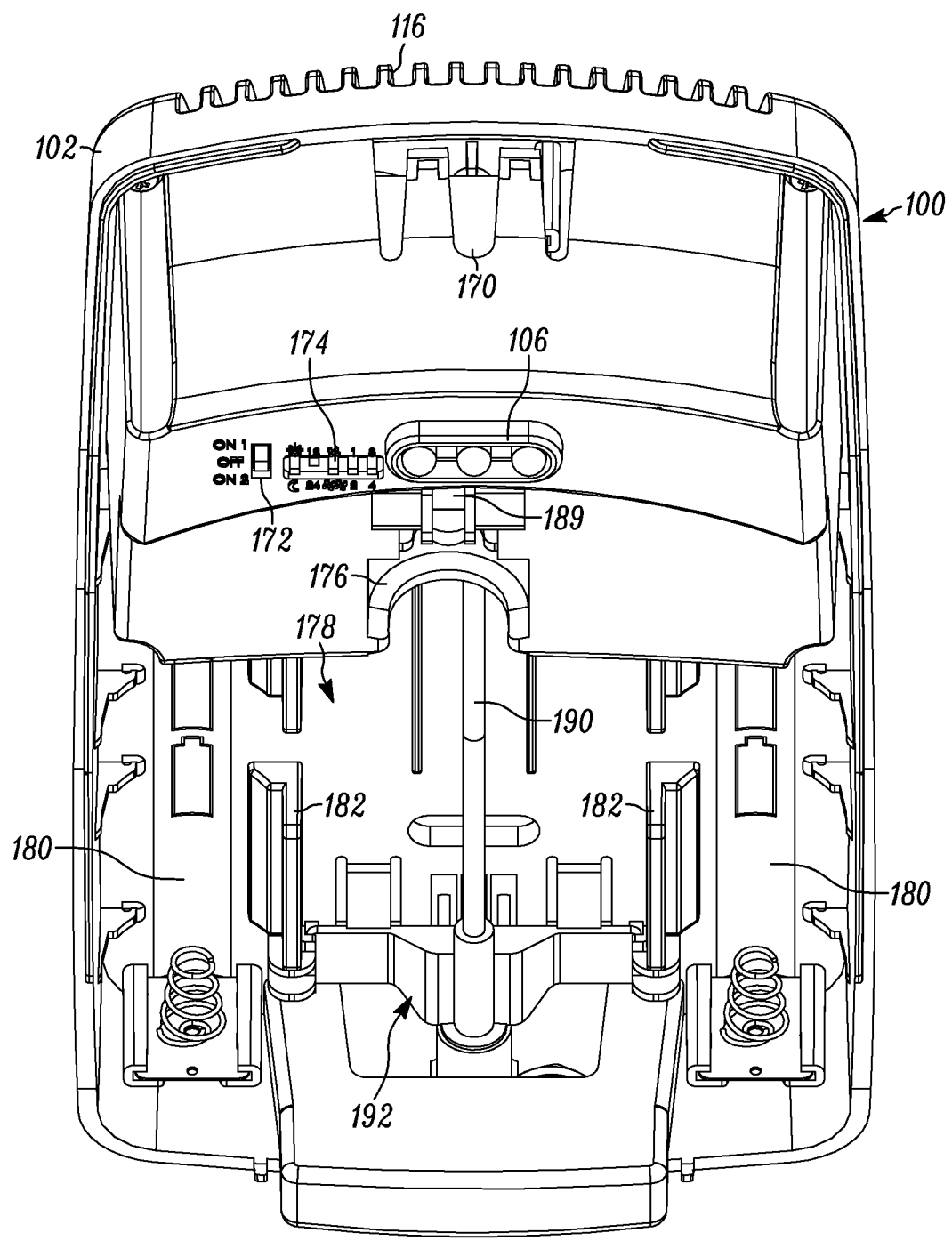
FIG. 7 illustrates a top perspective view of the dispenser of FIG. 1 with a direct output module installed.

Referring now to FIG. 7, a top perspective view of the dispenser 100 with the housing cover 104 removed and without a reservoir installed is shown. As shown, the dispenser housing 102 includes an upper latch 170 for engaging a mating portion on the housing cover 104. A fan on/off switch 172 and a dipswitch panel 174 are utilized to configure solution dosing frequency and fan activation (discussed below). The dispenser housing 102 further includes a neck receiver 176 to receive the solution container neck 146 and to assist with proper positioning and securement of the container assembly 122 inside a dispenser chamber 178 of the dispenser 100. A pair of battery compartments 180 are provided on either side of the dispenser chamber 178, the chambers 178 formed at least in part by battery supports 182. Additional or alternate power sources can be utilized as well, such as a 120 VAC, using a step-down transformer (not shown) positioned in a modified space inside the dispenser 100. As discussed above, the solution container 126 can include protrusions 156 and/or channels that are configured to matingly engage with mating channels or protrusions in the dispenser housing 102. A valve stem connector 189 is provided that secures to the pump valve assembly 128 to receive solution from the solution container 126. Additionally, a housing supply tube 190 is provided that communicates solution, pumped from the container 126, through the housing and to an output port, such as the primary output port 110 and/or the secondary output port 112.

Figure 8:
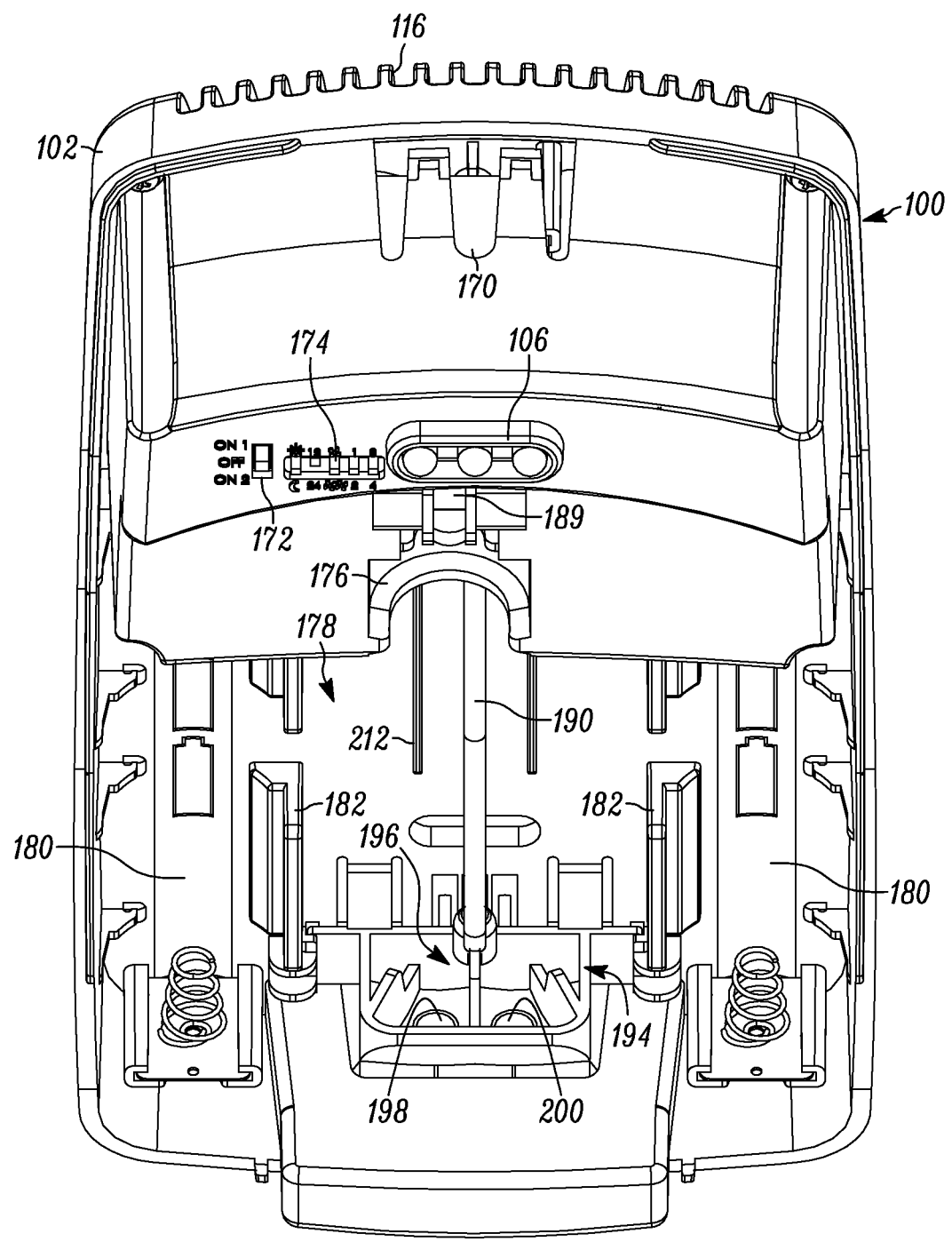
FIG. 8 illustrates a top perspective view of the dispenser of FIG. 1 with a reservoir module installed.

The dispenser 100 can be provided either with a direct output module 192 (FIG. 7) or a reservoir module 194 (FIG. 8). The direct output module 192 is configured to pass solution directly through the dispenser 100 as demanded. Such a configuration is utilized when the wick assembly 124 is not included to provide a source of fragrance for emission from the dispenser 100. When a purchaser of the product does not wish to capitalize on the wick assembly 124, they can purchase the dispenser 100 with the direct output module 192 along with a solution container 126 that lacks the wick assembly 124, and the system is ready to use. If a purchaser wishes to utilize the wick assembly 124 to provide a source of fragrance, they can easily remove the direct output module 192 and install the reservoir module 194 as seen in FIG. 8.

FIG. 8 illustrates another top perspective view of the dispenser of FIG. 1 with the reservoir module 194 installed in place of the direct output module 192. When the reservoir module 194 is utilized, the housing supply tube 190 extends to a reservoir 196 formed in the reservoir module 194. Solution pumped from the container assembly 122 is received and collected in the reservoir 196. When switching the reservoir module 194 for the direct output module 192, or vice-versa, the operator only has to remove the housing supply tube 190 from one module and re-install in the other module.

Figure 11:
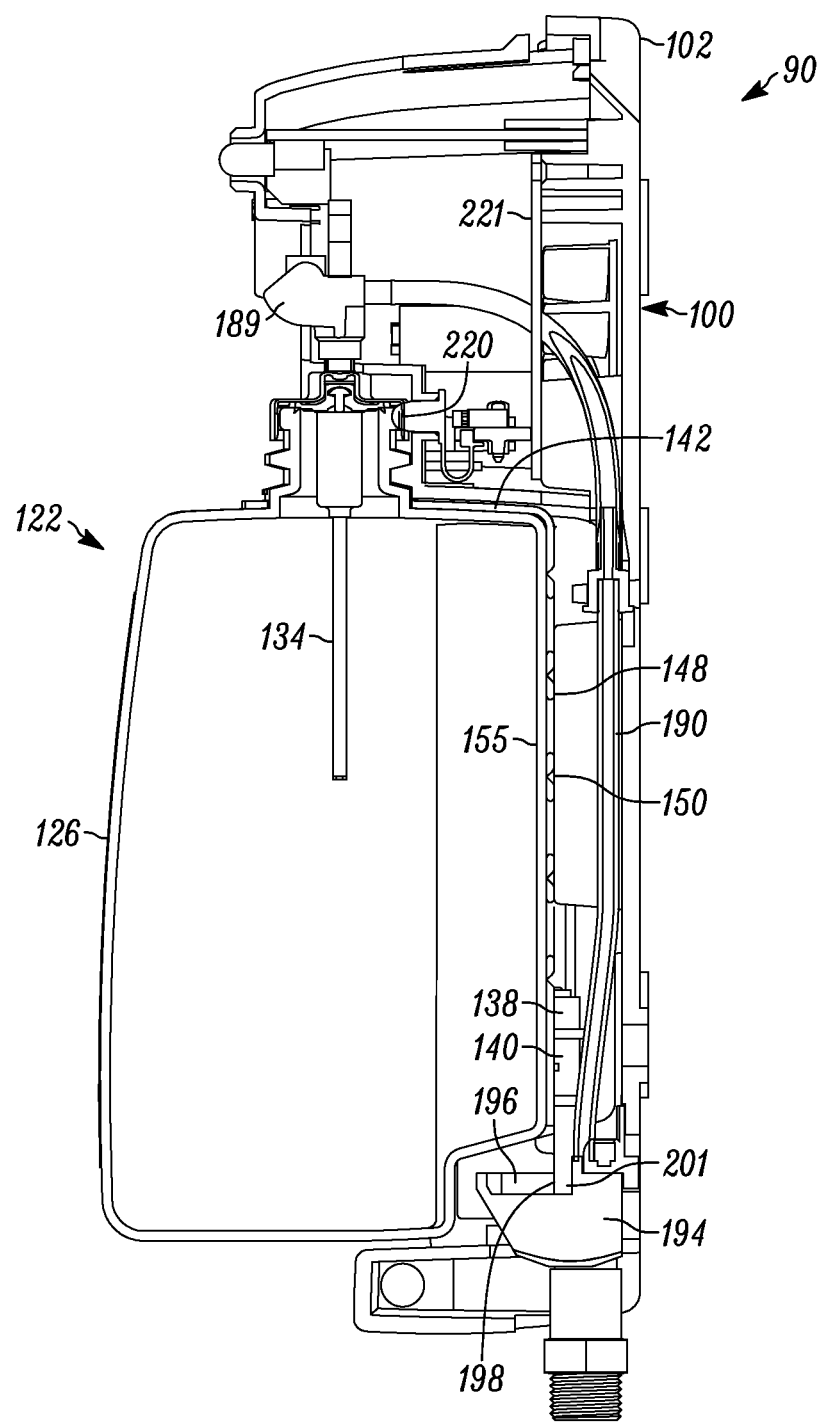
FIG. 11 illustrates a view similar to FIG. 10, but with the container assembly fully installed in the dispenser with the wick support structure in an installed position.

The reservoir module 194 includes one or more wick inlets, such as a primary wick inlet 198 and a secondary wick inlet 200. The wick inlets 198, 200 receive a wick bottom portion 201 of the wicks 136, 138 therein when wick assembly 124 is in its unfolded position (FIG. 11). Ridges 212 force wick assembly 124 into its unfolded position. When the wick bottom portion 201 of the wicks 136, 138 are positioned in the wick inlets 198, 200 and the solution includes a fragrance component, the fragrance situated in the reservoir 196 is absorbed by the wicks and travels up the wicks 136, 138 to provide an increased surface area for dispersing/emanating the fragrance.

Figure 9:
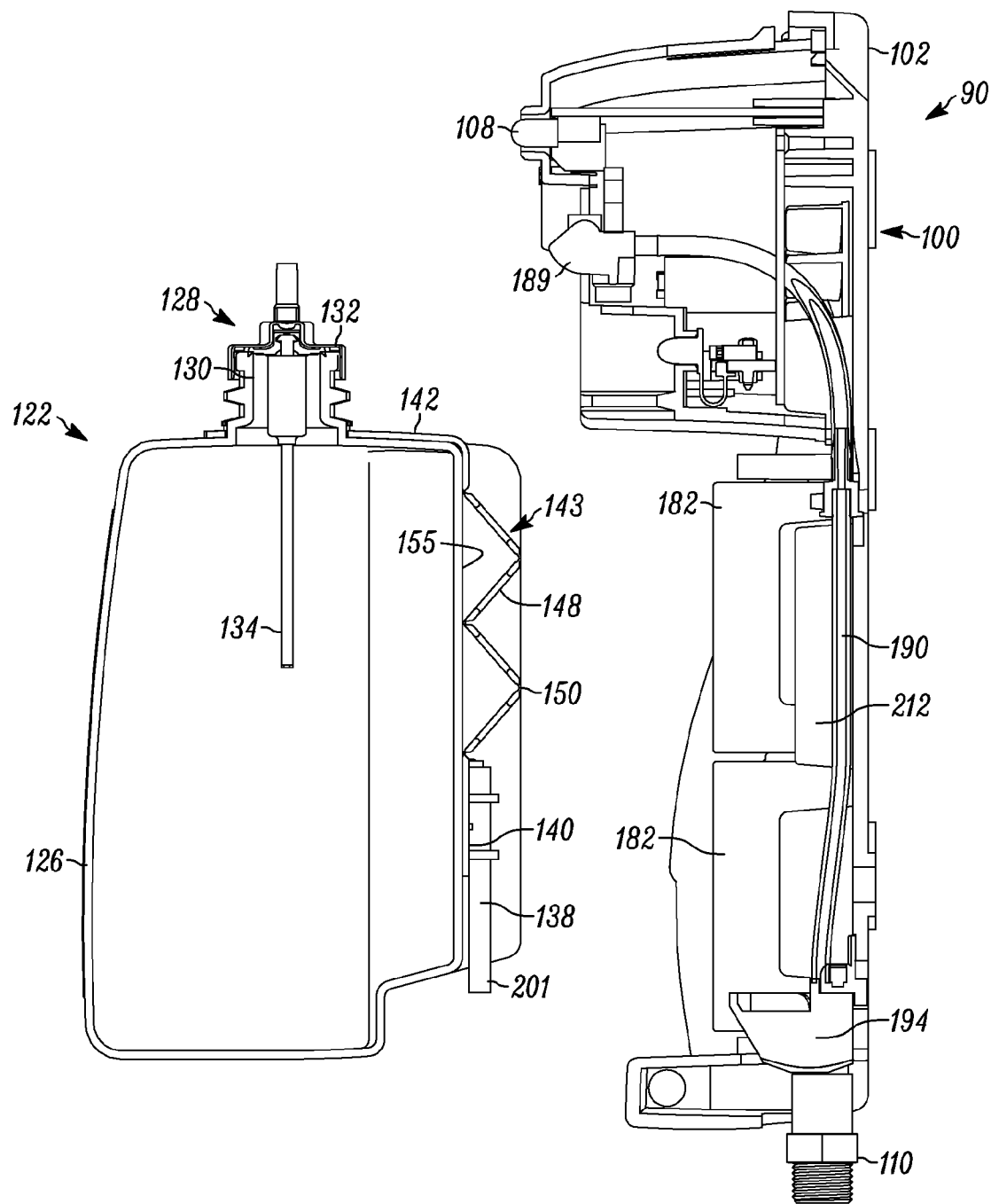
FIG. 9 illustrates a cross-sectional side view of the dispenser of FIG. 1 taken along line 1-1 of FIG. 11, with a housing cover removed; and a cross-sectional side view taken along line 5-5 of FIG. 5B of the container assembly 122.
Figure 10:
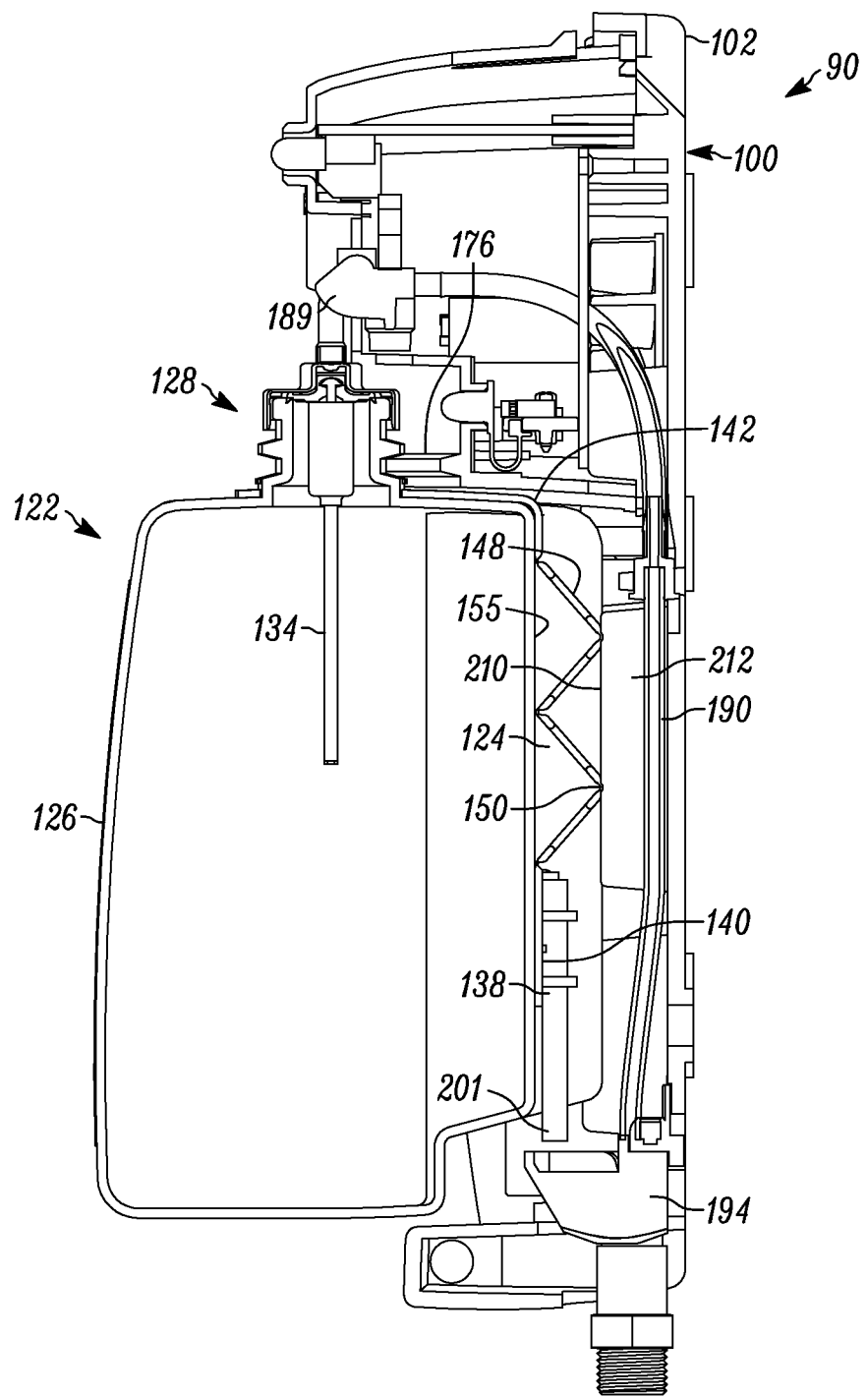
FIG. 10 illustrates a view similar to FIG. 9, but with the container assembly partially installed in the dispenser and the wick support structure in a non-installed position.

Referring now to FIG. 9, illustrated is a cross-sectional side view of the fixture cleaning and deodorizing apparatus 90 with the container assembly 122 removed from the dispenser 100. As the container assembly 122 is not installed in the dispenser 100, the wicks 136, 138 (along with the wick mount 140) remain in an upwards pre-installation position to allow clearance to install the container assembly 122. In addition, the spacers 148 remain in a partially folded position. FIG. 10 illustrates the fixture cleaning apparatus 90 with the container assembly 122 partially installed in the dispenser 100. As shown, the hinges 150 are in abutment with a front surface 210 of a pair of ridges 212 extending from the dispenser housing 102. The ridges 212 serve to push the spacers 148 into an unfolded position as the container assembly 122 is inserted into the dispenser chamber 178 of the dispenser 100. More particularly, with the spacers 148 sandwiched between the channel bottom portion 155 of the rear channel 153 and the front surface 210 of a pair of ridges 212, the wick mount 140 must move downwards to allow the spacers 148 to shift.

Figure 12:
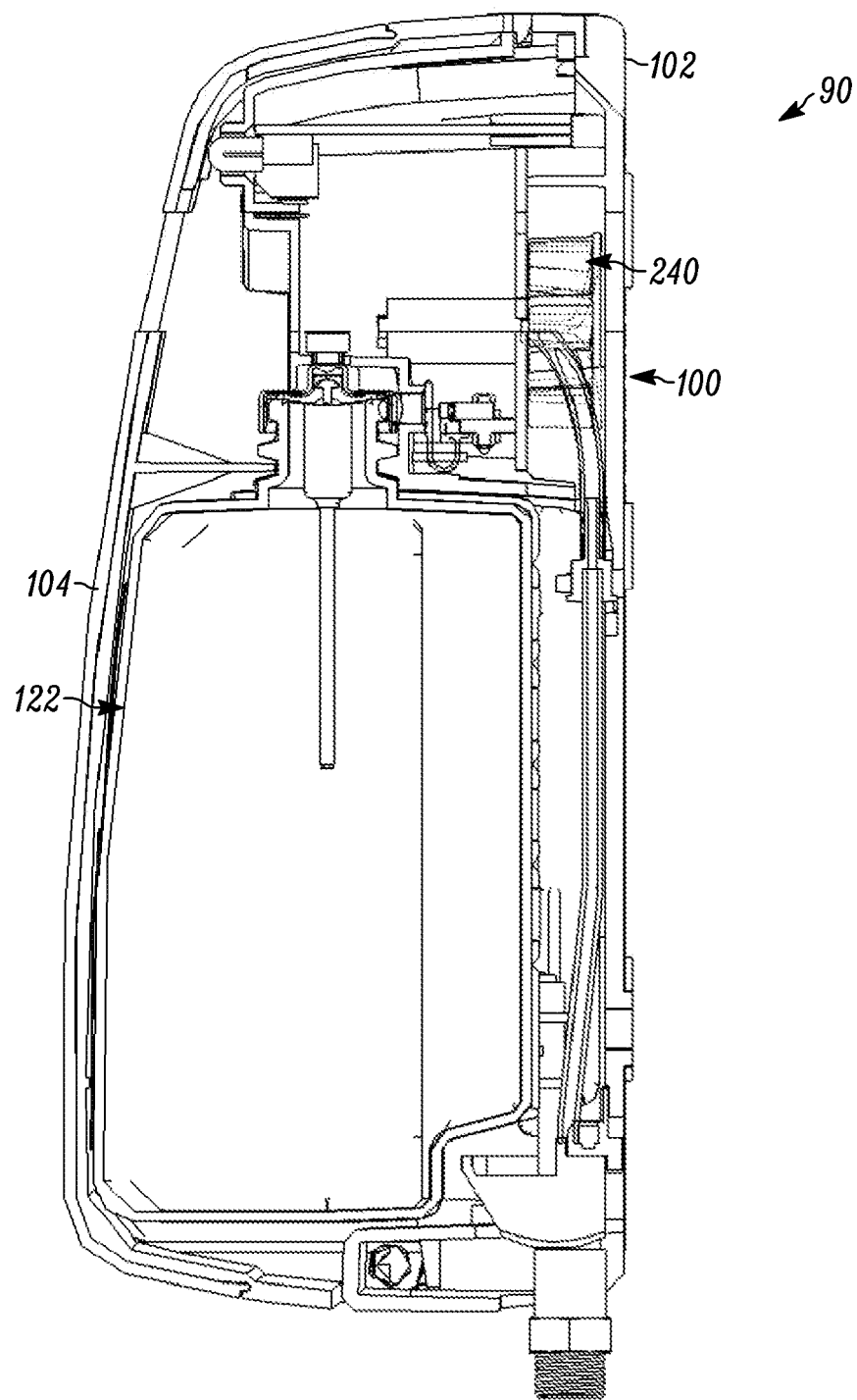
FIG. 12 illustrates a view similar to FIG. 11, but with the housing cover in a closed position.

FIG. 11 illustrates the fixture cleaning apparatus 90 with the container assembly 122 fully installed in the dispenser 100. As shown, the spacers 148 have been pushed flat against the channel bottom portion 155 of the rear channel 153 and the wick mount 140 has shifted downwards along with the wicks 136, 138 such that the wick bottom portion 201 of the wicks 136, 138 are positioned in the primary wick inlet 198 and secondary wick inlet 200. In addition, pushing the solution container 126 in place causes an abutment of the solution container 126 with a reset switch 220 to communicate to a processor (not shown) mounted on a printed circuit board 221, that a refill has been installed. FIG. 12 illustrates the fixture cleaning and deodorizing apparatus 90 with the housing cover 104 installed and fan assembly 240 visible. Using close tolerances, the ability to close the housing cover 104 properly can be used as an indication that the container assembly 122 has been fully installed in the dispenser 100, since without a full flattening of the spacers 148 extra space between the channel bottom portion 155 of the rear channel 153 would exist.

Removal of the container assembly 122 also removes the complete wick assembly 124 with the wicks 136, 138 intact, thereby eliminating the hassle and mess of separately removing the wicks and ensuring that the wicks are replaced with each refill of solution to prevent failure inducing degradation and potential overflowing of reservoir 196. In this regard, the overall reliability, longevity, and effectiveness of the fixture cleaning and deodorizing apparatus 90 is substantially enhanced. As noted, the container assembly 122 need not include the wick assembly 124.

Figure 13:
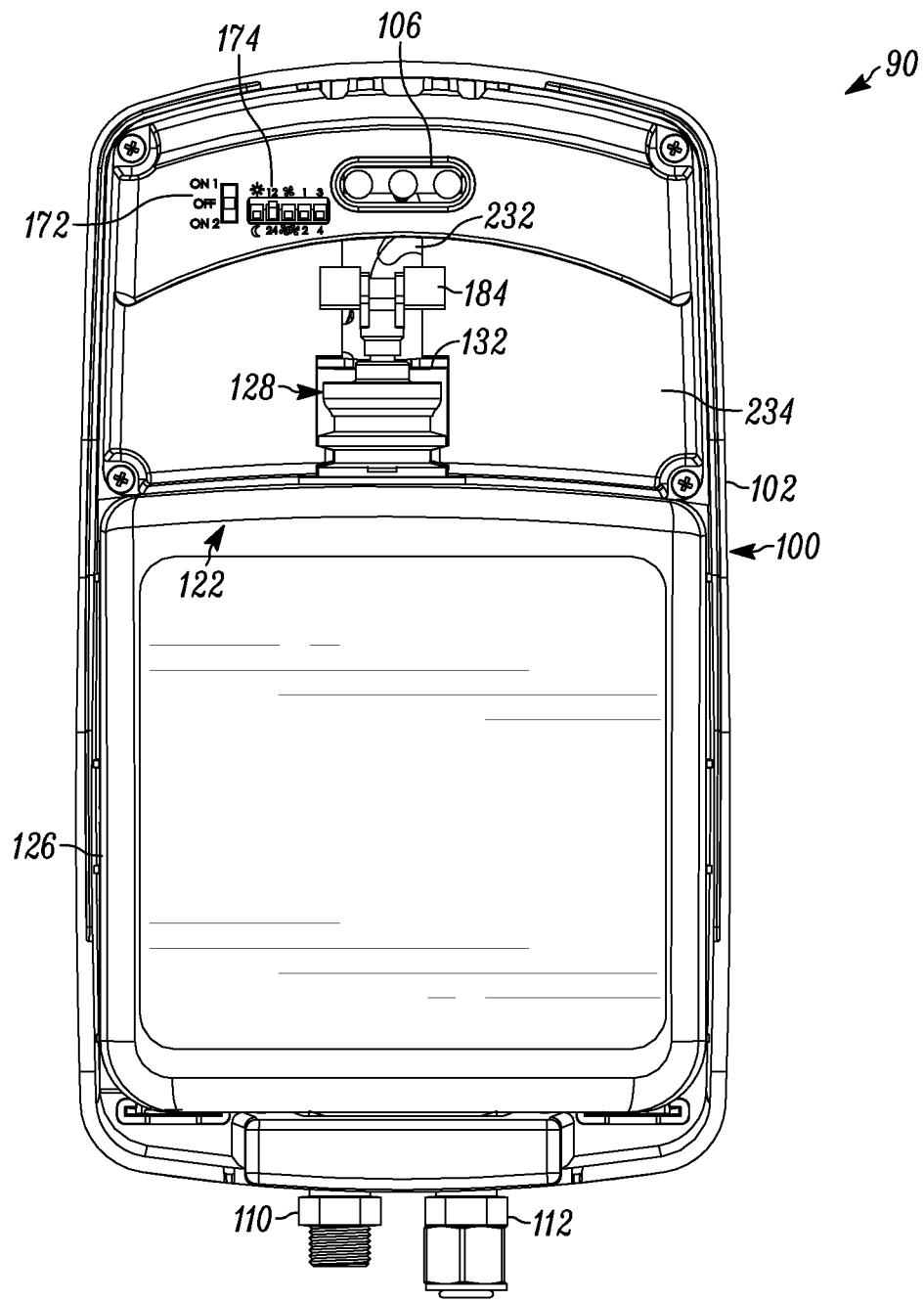
FIG. 13 illustrates a front view of the fixture cleaning and deodorizing apparatus with the housing cover removed.
Figure 14:
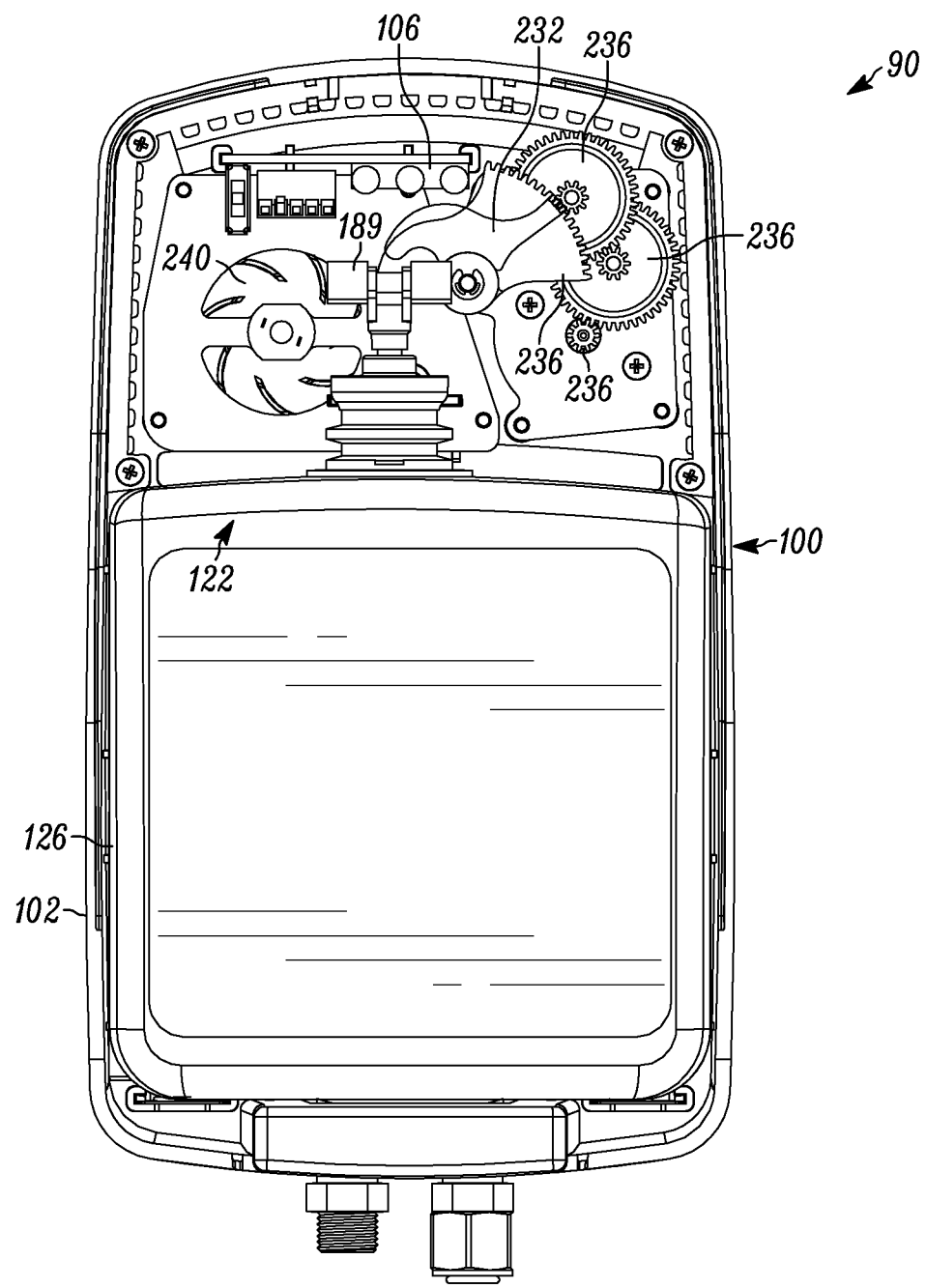
FIG. 14 illustrates a front view of the fixture cleaning and deodorizing apparatus with a gear cover removed.
Figure 15:
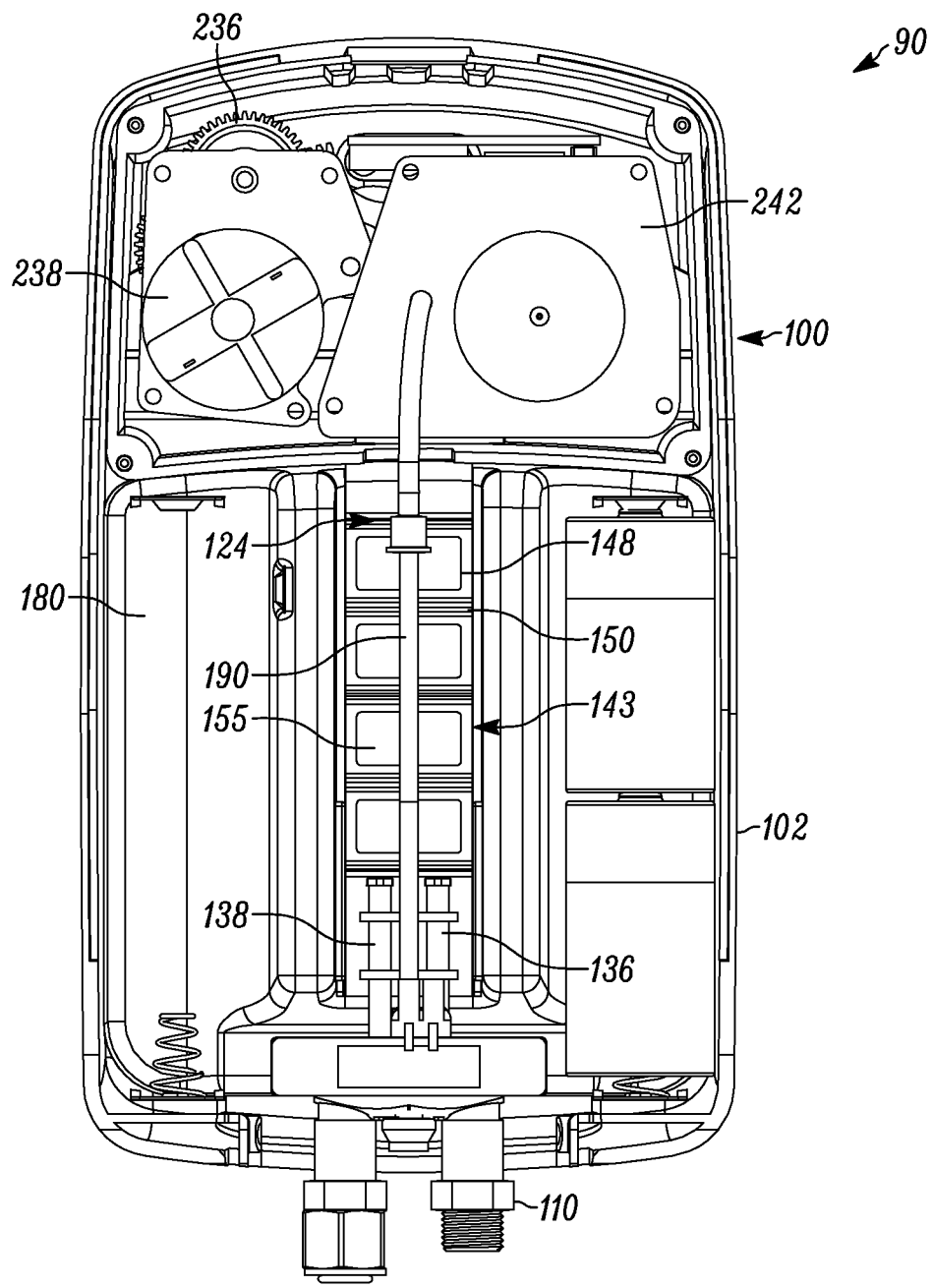
FIG. 15 illustrates a cross-section rear view of the fixture cleaning and deodorizing apparatus taken at line 2A-2A of FIG. 2.

FIG. 13 illustrates a front view of the fixture cleaning apparatus 90 with the housing cover 104 removed, showing the valve stem connector 189 secured to the pump valve assembly 128. The valve stem connector 189 is configured to receive force from a hammer 232, which depresses the valve stem connector 189 and subsequently actuates the pump valve assembly 128, thereby pumping solution from the solution container 126 through the valve stem connector 189 and into the housing supply tube 190. Gear cover 234 is covering gears 236. FIG. 14 illustrates a front view of the apparatus 90 with the housing cover 104 and gear cover 234 (FIG. 13) removed. The hammer 232 is driven by one or more gears 236, which are powered by an electric motor 238 (FIG. 15). Actuation of the motor 238 results in rotation of the hammer 232.

Figure 16:
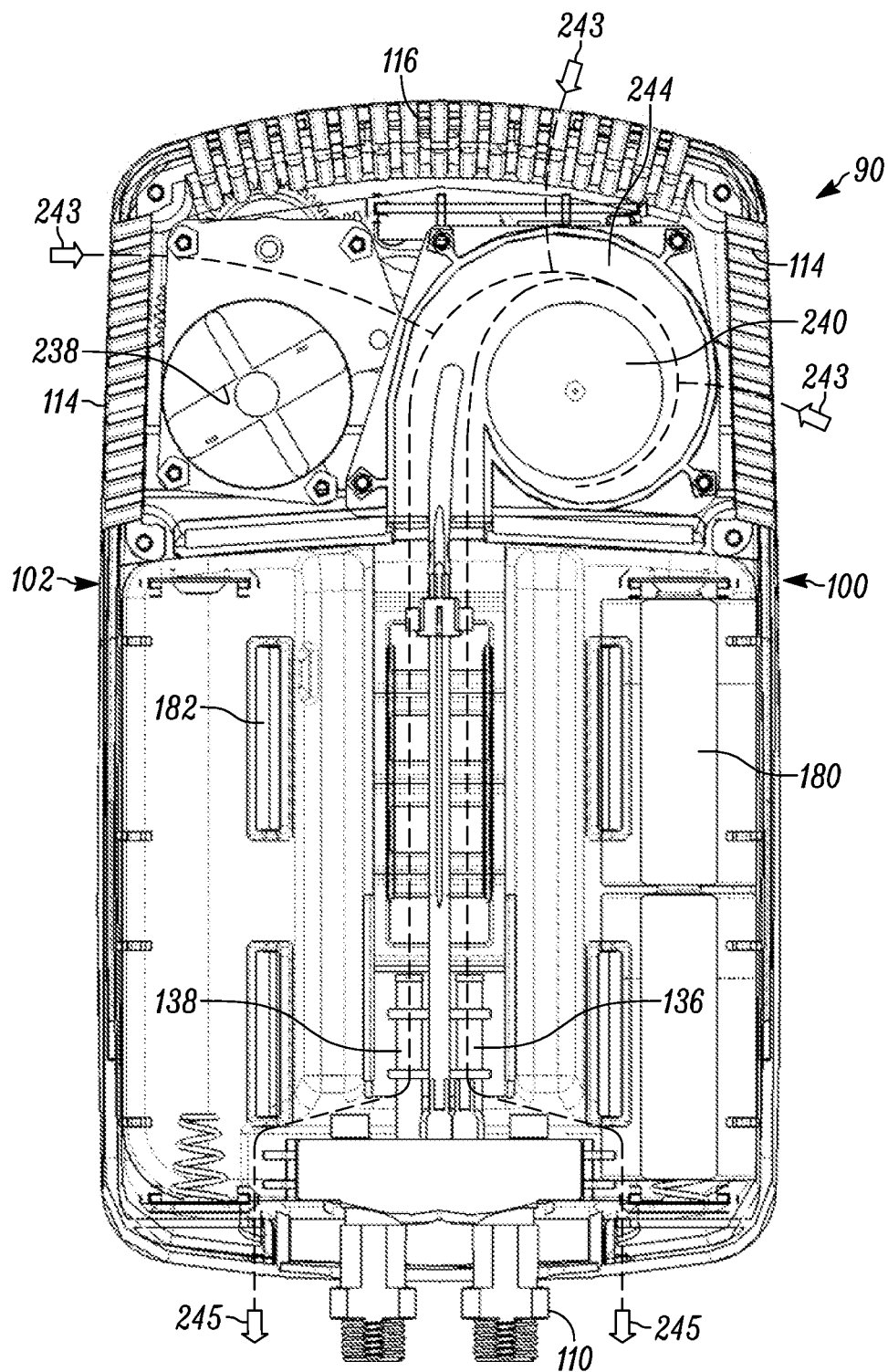
FIG. 16 illustrates a cross-section rear view of the fixture cleaning and deodorizing apparatus taken at line 2B-2B of FIG. 2.
Figure 17:
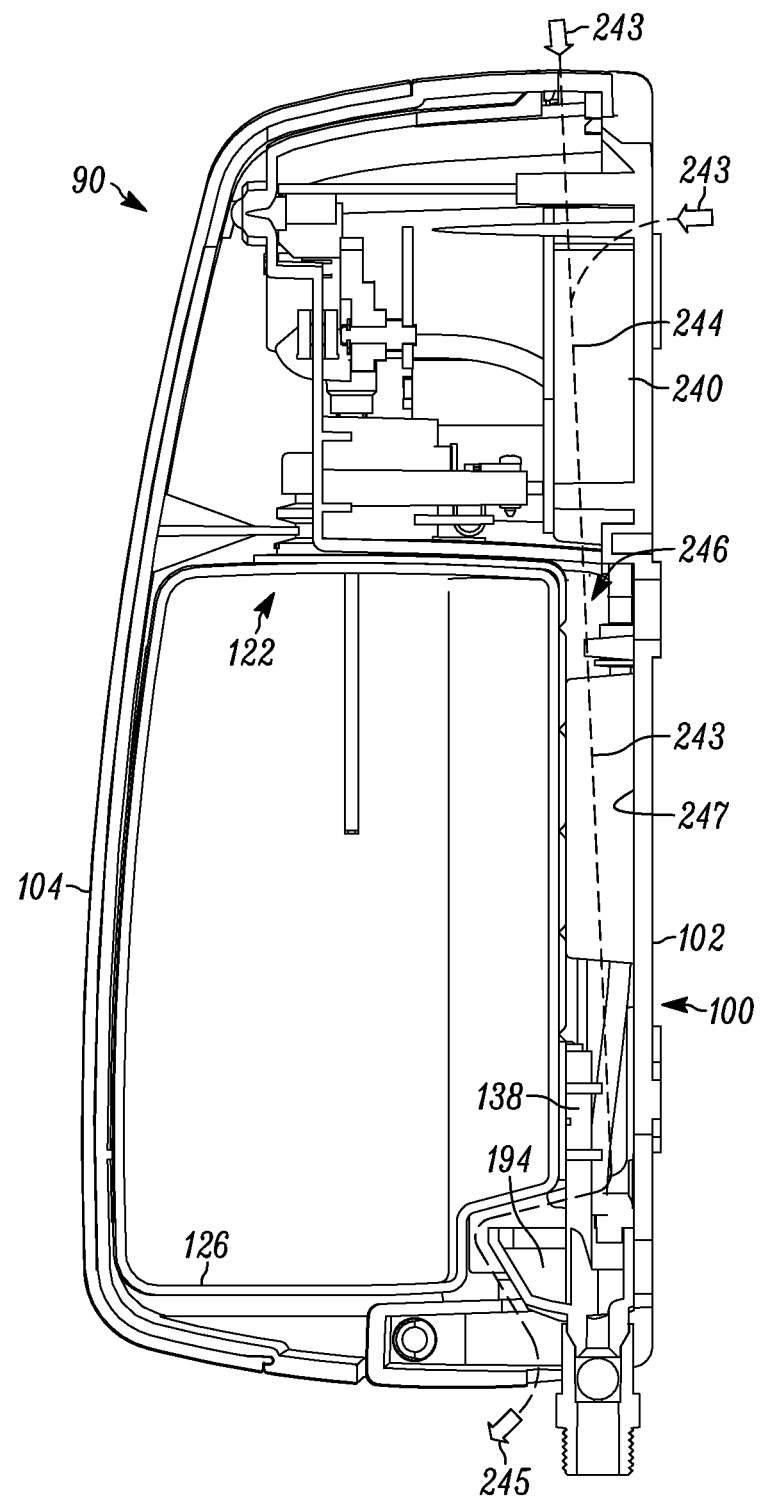
FIG. 17 illustrates a partial cross-sectional side view of the fixture cleaning and deodorizing apparatus of FIG. 1, taken along line 1-1 of FIG. 1.

Although a wick-containing reservoir system can provide a suitable fragrance distribution system, a fan assembly 240 can be provided, such as a squirrel-cage fan assembly, to enhance emanation/dispersion of fragrance from the wicks 136, 138. FIG. 15 illustrates a cross-section rear view of the apparatus 90 taken at line 2A-2A of FIG. 2. As seen in FIG. 15, a fan cover 242 is provided to seal one side of a fan blade chamber 244 (FIG. 16). Referring to FIG. 16, provided is a cross-section rear view of the apparatus 90 taken at line 2B-2B of FIG. 2 with the fan cover 242 removed for clarity. When activated, the fan assembly 240 pulls fresh air through the side intake vents 114 and top intake vents 116. The fresh air 243 is pushed through the fan blade chamber 244 (FIG. 17) and downwards into a fan passage 246 (FIG. 17) that includes various portions of the fixture cleaning and deodorizing apparatus 90, such as, an inner back portion 247 (FIG. 17) of the dispenser housing 102, the rear channel 153, the solution container 126, and the housing cover 104. As the fresh air 243 is directed past the wicks 136, 138 and the reservoir 196, the scent of the solution is forced out of the fixture cleaning apparatus 90 as scented air 245 and into the room that the apparatus 90 occupies. Use of the fan assembly 240 in this regard allows for enhanced dispersion of scent. FIG. 17 illustrates a partial cross-sectional side view of the apparatus 90, taken along line 1-1 of FIG. 1. FIG. 17 further illustrates the path of the fresh air 243 through the fixture cleaning apparatus 90.

Figure 18:
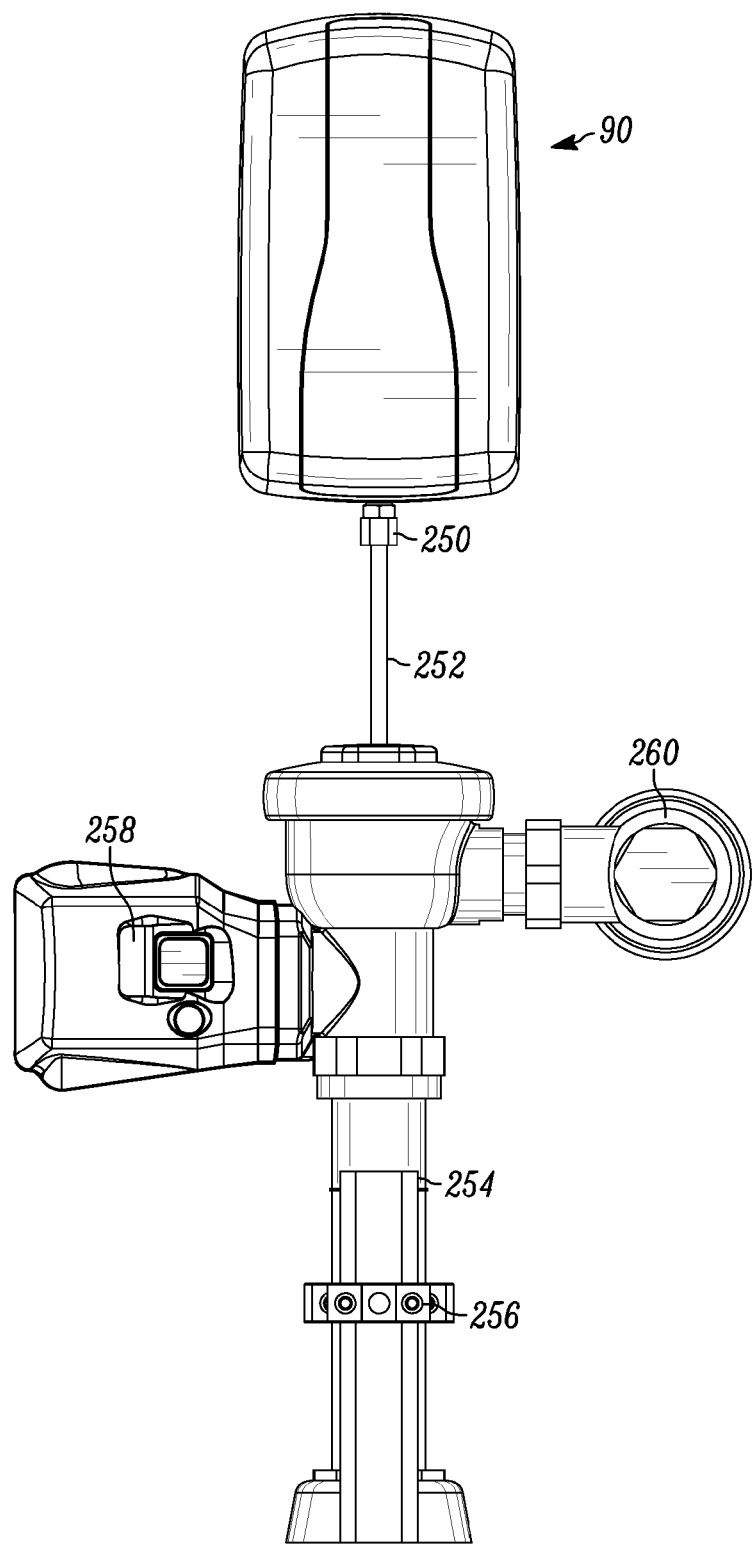
FIG. 18 illustrates a view of the fixture cleaning and deodorizing apparatus connected to water supply piping.

FIG. 18 illustrates a view of the fixture cleaning and deodorizing apparatus 90 with only a single output port 250, which is connected to piping for a toilet/urinal. More particularly, the output port 250 is connected to an output line 252, which is connected to a spurge pipe 254 via a saddle valve 256. An auto-flush valve 258 is shown that controls the flow of the water from the supply pipe 260 into the spurge pipe 254. Flushing of the fixture creates a drop in pressure in the output line 252, which allows a metered amount of solution to be released into the output line 252, as solution already present in the output line 252 is pulled into the spurge pipe via suction created at the spurge pipe 254. It is to be understood that the apparatus 90 need not be connected to a spurge pipe 254, it can be connected to other water supply piping or the directly to the fixture itself, including being supported adjacent to the fixture to provide the solution via gravity feed.

In use, when a solution container 126 is empty as indicated by the indicators 106, the housing cover 104 is lifted and the container assembly 122 is removed from the dispenser 100. A new container assembly 122 is installed in the dispenser chamber 178 of the dispenser 100 and the lid is closed. Installation of the new container assembly 122 pushes the reset switch 220, which communicates to the processor that a new container assembly 122 has been installed. The spacers 148 and/or hinges 150 are pushed against the ridges 212 to flatten the spacers 148 and push the wick mount downwards, inserting the bottom portions 201 of the wicks 136, 138 into the wick inlets 198, 200.

Dispersion of the solution from the apparatus 90 can occur based on a number of criteria, such as scheduled time, a dark room sensed, a flush sensed, etc. These criteria are provided and managed by the dipswitch panel 174 on the printed circuit board 221. When the fixture cleaning and deodorizing apparatus 90 is activated to disperse the solution, the processor activates the hammer 232 to push down the valve stem connector 189 on the pump valve assembly 128. Actuation of the pump valve assembly 128 pumps solution through the container supply tube 134 and into the housing supply tube 190. At the same time, solution that was in the housing supply tube 190 is pumped into the reservoir 196. Further, solution that resided in the reservoir 196 is pulled through an outlet port (110, 112, 250), which is connected to an output line (252), which is connected to a spurge pipe 254. Finally, the solution in the spurge pipe 254 is pulled into the fixture. Although some fragrance (when included in the solution) will emanate from the solution, as the solution enters and is processed by the fixture, the majority of emanation will come from the wicks 136, 138. As noted above, when a fan assembly 240 is provided, the fan can be activated by a flushing of the fixture or on a scheduled basis or sensed basis. As the wicks 136, 138 are continuously soaked with solution (with fragrance), the fan assembly 240 can be operated at any time to emanate a scent from the fixture cleaning apparatus 90.

In at least some embodiments, the fixture cleaning and deodorizing apparatus 90 can be utilized solely as an air freshener/deodorizer. As such the output ports 110, 122 can be plugged or otherwise non-existent. The solution would include only a fragrance and/or deodorizer that is delivered to a reservoir similar to reservoir 196 and absorbed by one or more wicks, such as wicks 136, 138. By utilizing the fan assembly 240, the apparatus 90 can provide a sufficient airflow to function as an air freshener/deodorizer.

The shape and size of the aforementioned components can be modified to accommodate installation space requirements, desired level of solution processing and fragrance emanation, etc. In addition, the described location of components of the fixture cleaning and deodorizing apparatus 90 can be modified to accommodate various shapes and sizes of the fixture cleaning and deodorizing apparatus 90 and/or to improve efficiency. The spacers 148 can be formed from various materials, such as a wick material or plastic that is configured in any of numerous shapes and sizes. The wicks 136, 138 can be secured to the wick mount in any one of numerous ways, such as protruding rings 125 (FIG. 5B) that allow for insertion of the wicks 136, 138 in a vertical orientation. Also, when a single wick is used, the wick mount can be modified to provide a centered mounting point for the wick.

If the solution container 126 is a liner/bag, can affix the wicks 136, 138 to the solution container 126 (tape, glue, etc.) on a back side of the solution container 126. The male plastic features (similar to parts 212 on FIG. 10) can push in the flexible bag accordingly (with the closer of the main cover 104) and therefore, also push down the wicks 136, 138 into place in the reservoir.

Additionally, the spacer 148, hinge 150, and wick mount 140 configuration used to shift the wicks into the wick inlets 198, 200 can be replaced with other configurations, such as a flexible arc-shaped rod that is secured to an upper portion of the rear channel 153 and a wick holder at a lower portion of the rear channel 153, wherein the arc of the rod is collapsed when abutted with the ridges 212 or the dispenser housing 102, to push the wick holder downwards. Further, the components can be substituted with other components that perform a similar function, such as a different style of fan.

It is specifically intended that the fixture cleaner and deodorizing apparatus and method of use not be limited to the embodiments and illustrations contained herein, but include modified forms of those embodiments including portions of the embodiments and combinations of elements of different embodiments as come within the scope of the following claims.

We claim:

1. A fixture cleaning and deodorizing dispenser comprising:
    a dispenser housing;
    a housing cover securable to the dispenser housing;
    a housing supply tube;
    a dispenser chamber configured to receive a solution container, the solution container comprising a rear wick assembly receiving channel;
    a reservoir module for receiving one or more wicks, wherein the one or more wicks are secured in a wick assembly, wherein the wick assembly comprises
        a plurality of spacers secured together to form a collapsible wick support structure,
        a neck mount portion secured to a first end of the wick support structure, the neck mount portion configured to secure to the solution container,
        the one or more wicks, and
        a wick mount secured to a second end of the wick support structure, the wick mount configured to secure the one or more wicks thereto;
    one or more ridges formed with or secured to the dispenser housing;
    one or more battery compartments;
    a printed circuit board;
    a hammer for at least indirectly engaging a valve assembly of a solution container; and
    an output port in communication with the housing supply tube.

2. The dispenser of claim 1, wherein the reservoir module includes one or more wick inlets.

3. The dispenser of claim 1, wherein the wick assembly is slidably attached to the solution container.

4. The dispenser of claim 1, further comprising a fan assembly configured to direct airflow through the dispenser housing.

5. The dispenser of claim 1, further comprising a direct output module.

6. The dispenser of claim 1, wherein the hammer is activated by a plurality of gears.

7. The dispenser of claim 1, further comprising an indicator group comprising at least one indicator component selected from the group consisting of an LED, a sensor, and combinations thereof.

8. A wick assembly comprising:
    a plurality of spacers secured together with hinges to form a collapsible wick support structure;
    a neck mount portion secured to a first end of the wick support structure, the neck mount portion configured to secure to a solution container;
    one or more wicks; and
    a wick mount secured to a second end of the wick support structure, the wick mount configured to secure the one or more wicks thereto.

9. The wick assembly of claim 8, wherein the wick assembly is secured on a container assembly, the container assembly comprising:
    a solution container for housing a solution, the solution container comprising
        a container neck, and
        a rear wick assembly receiving channel;
    a container supply tube;
    a pump; and
    a pump valve assembly.

10. A method of wick replacement for a fixture cleaner apparatus comprising:
    accessing a dispenser chamber of a dispenser;
    removing a first container assembly from the dispenser chamber;
    installing a second container assembly in the dispenser chamber, wherein the second container assembly includes a rear channel extending along a back of the solution container;
    providing a wick assembly comprising a plurality of spaces secured together with hinges to form a collapsible wick support structure and a neck mount portion secured to a first end of the wick support structure, the neck mount portion configured to secure to the solution container, the wick assembly further having one or more wicks and a wick mount secured to a second end of the wick support structure and configured to secure the one or more wicks thereto; and
    actuating the plurality of spacers hingedly secured together to push the wicks downward along the rear channel.

11. The method of claim 10 further comprising actuating a fan assembly to provide airflow past the wicks.

12. The method of claim 10 further comprising physically contacting a reset switch with the second container assembly.

13. The method of claim 12 further comprising communicating the presence of the second container assembly to a processor.

14. The method of claim 13 further comprising resetting at least one indicator selected from the group consisting of an LED and a sensor.

15. A wick assembly comprising:
    a plurality of spacers secured together to form a collapsible wick support structure;
    a neck mount portion secured to a first end of the wick support structure, the neck mount portion configured to secure to a solution container;
    one or more wicks; and
    a wick mount secured to a second end of the wick support structure, the wick mount configured to secure the one or more wicks thereto,
    wherein the wick assembly is secured on a container assembly, the container assembly comprising
    a solution container for housing a solution, the solution container comprising
        a container neck, and
        a rear wick assembly receiving channel;
    a container supply tube;
    a pump; and
    a pump valve assembly.

16. The wick assembly of claim 15, wherein the plurality of spacers are secured together with hinges.

* * * * *